United States Patent
Brannan

(10) Patent No.: US 11,259,860 B2
(45) Date of Patent: Mar. 1, 2022

(54) SYSTEMS AND METHODS FOR PROVIDING SENSORY FEEDBACK WITH AN ABLATION SYSTEM

(71) Applicant: COVIDIEN LP, Mansfield, MA (US)

(72) Inventor: Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 743 days.

(21) Appl. No.: 15/714,593

(22) Filed: Sep. 25, 2017

(65) Prior Publication Data

US 2019/0090929 A1  Mar. 28, 2019

(51) Int. Cl.
  *A61B 18/12* (2006.01)
  *A61B 18/18* (2006.01)
  (Continued)

(52) U.S. Cl.
  CPC .......... *A61B 18/1206* (2013.01); *A61B 18/14* (2013.01); *A61B 18/1815* (2013.01);
  (Continued)

(58) Field of Classification Search
  CPC . A61B 18/1206; A61B 18/14; A61B 18/1815; A61B 2017/00128; A61B 2017/00973; A61B 2018/00577; A61B 2018/00589; A61B 2018/00601; A61B 2018/00648; A61B 2018/00666; A61B 2018/00678; A61B 2018/00702; A61B 2018/0072; A61B 2018/00779; A61B 2018/00785; A61B 2018/00791; A61B 2018/00827; A61B 2018/00875; A61B 2018/00886; A61B 2018/00892;
  (Continued)

(56) References Cited

U.S. PATENT DOCUMENTS

| | | |
|---|---|---|
| 7,364,578 B2 | 4/2008 | Francischelli et al. |
| 8,221,418 B2 | 7/2012 | Prakash et al. |
| | (Continued) | |

FOREIGN PATENT DOCUMENTS

| | | |
|---|---|---|
| EP | 3192461 A1 | 7/2017 |
| WO | 2012018821 A2 | 2/2012 |

OTHER PUBLICATIONS

Extended European Search Report issued in corresponding Appl. No. EP 18196075.8-1124 dated Dec. 11, 2018 (7 pages).

(Continued)

*Primary Examiner* — Tigist S Demie
(74) *Attorney, Agent, or Firm* — Carter, DeLuca & Farrell LLP

(57) ABSTRACT

A surgical system includes a power supply, a power stage coupled to the power supply for converting electric energy to a power signal, an audio output device, a sensor, and a controller coupled to the power supply, the power stage, and the audio output device. The controller is operably coupled to the sensor. The power stage is configured to transmit the power signal to a surgical instrument such as an electrosurgical instrument or a microwave instrument. The sensor may be disposed on the surgical instrument. The controller causes the audio output device to output sensory feedback during operation of the surgical generator based on sensor signals received from the sensor during a surgical procedure.

20 Claims, 6 Drawing Sheets

(51) Int. Cl.
*A61B 18/14* (2006.01)
*A61B 17/00* (2006.01)
*A61B 18/00* (2006.01)
*A61B 90/00* (2016.01)

(52) U.S. Cl.
CPC ............ *A61B 2017/00128* (2013.01); *A61B 2017/00973* (2013.01); *A61B 2018/0066* (2013.01); *A61B 2018/0072* (2013.01); *A61B 2018/00577* (2013.01); *A61B 2018/00589* (2013.01); *A61B 2018/00601* (2013.01); *A61B 2018/00648* (2013.01); *A61B 2018/00678* (2013.01); *A61B 2018/00702* (2013.01); *A61B 2018/00779* (2013.01); *A61B 2018/00785* (2013.01); *A61B 2018/00791* (2013.01); *A61B 2018/00827* (2013.01); *A61B 2018/00875* (2013.01); *A61B 2018/00886* (2013.01); *A61B 2018/00892* (2013.01); *A61B 2018/00898* (2013.01); *A61B 2018/00922* (2013.01); *A61B 2018/00928* (2013.01); *A61B 2018/128* (2013.01); *A61B 2018/1823* (2013.01); *A61B 2090/064* (2016.02)

(58) Field of Classification Search
CPC ........... A61B 2018/00898; A61B 2018/00922; A61B 2018/00928; A61B 2018/128; A61B 2018/1823
See application file for complete search history.

(56) References Cited

U.S. PATENT DOCUMENTS

| | | |
|---|---|---|
| 8,920,421 B2 | 12/2014 | Rupp |
| 2006/0229594 A1* | 10/2006 | Francischelli ........... A61N 7/02 606/27 |
| 2008/0200861 A1* | 8/2008 | Shalev .................... A61Q 9/04 604/20 |
| 2009/0138011 A1* | 5/2009 | Epstein .............. A61B 18/1233 606/42 |
| 2010/0286681 A1* | 11/2010 | Podhajsky ......... A61B 18/1815 606/33 |
| 2011/0118720 A1* | 5/2011 | Turner ............... A61B 18/1815 606/33 |
| 2011/0224668 A1* | 9/2011 | Johnson ............. A61B 18/1233 606/42 |
| 2012/0078139 A1 | 3/2012 | Aldridge et al. |
| 2016/0000302 A1 | 1/2016 | Brown et al. |
| 2016/0074092 A1 | 3/2016 | Joseph |
| 2016/0317229 A1 | 11/2016 | Girotto et al. |

OTHER PUBLICATIONS

European Examination Report issued in corresponding Appl. No. EP 18196075.8 dated Dec. 3, 2020 (6 pages).

* cited by examiner

SYSTEMS AND METHODS FOR PROVIDING SENSORY FEEDBACK WITH AN ABLATION SYSTEM

BACKGROUND

Technical Field

The present disclosure is directed to systems and methods for ablating tissue. More specifically, the present disclosure is directed to a system for generating auditory feedback during a surgical procedure.

Description of Related Art

During a surgical procedure, it may be desirable to cut, coagulate, desiccate, or ablate target tissue by delivering energy to the target tissue. Surgical procedures which involve delivering energy to target tissue often involve delivering an electrical current (e.g., radio-frequency (RF) energy) via one or more electrosurgical devices, including ablation or electrocautery devices. The electrosurgical devices are generally configured to deliver either monopolar or bipolar energy via an electrode or radiator located on the electrosurgical device as the electrode or radiator comes into contact with target tissue.

A clinician may set the amount of energy to be applied to target tissue or the desired energy waveform prior to the surgical procedure. Additionally, the clinician may increase or decrease the energy applied or change the waveform generated as desired during the surgical procedure. As energy is applied to the tissue, the clinician monitors the tissue ablation directly during non-minimally invasive procedures or indirectly via an imaging system. Tissue properties, such as temperature, width, and impedance, may be monitored by one or more sensors associated with the electrosurgical device and transmitted to a controller which can vary the applied energy.

SUMMARY

Accordingly, it is desirable to provide information associated with the ablation procedure via audio signals.

In accordance with an aspect of the present disclosure, an electrosurgical generator includes a power supply, a power stage coupled to the power supply for converting electrical power to electrosurgical energy, an audio output device, an electrosurgical instrument sensor, and a controller. The power stage is configured to transmit power to an electrode or radiator of an electrosurgical instrument. The controller is coupled to the power supply, the power stage, the audio output device, and further operably coupled to the electrosurgical instrument sensor. The controller causes the audio output device to output sensory feedback during operation of the electrosurgical generator based on sensor signals received from the power stage or the electrosurgical instrument sensor as electrosurgical energy is applied to tissue during a surgical procedure.

The sensory feedback may include audio signals. In aspects, the sensory may include a first audio signal and a second audio signal. The controller may receive sensor signals from the electrosurgical instrument sensor indicative of a property selected from the group consisting of tissue temperature, instrument temperature, tissue impedance, tissue permittivity, tissue permeability, tissue elasticity, force applied to an electrosurgical instrument, current sourced by an electrode, voltage applied to an electrode, energy delivered by a radiator, energy reflected from a radiator, power delivered to a radiator, and power reflected from a radiator.

The controller may be configured to monitor a duration of time during a surgical procedure and output sensory feedback based on the monitored duration of time. In response to determining that the duration of time is greater than a predetermined threshold, the controller may transmit control signals to the audio output device to output audio signals at a first frequency and a second frequency.

In accordance with aspects of the present disclosure, an electrosurgical generator includes a power supply, a power stage coupled to the power supply, an audio output device, an electrosurgical instrument sensor, and a controller. The power stage converts electrical power to electrosurgical energy. The power stage is configured to transmit power to an electrode or radiator of an electrosurgical instrument. The controller is coupled to the power supply, the power stage, the audio output device, and is operably coupled to the electrosurgical instrument sensor. The controller causes the audio output device to output first sensory feedback and second sensory feedback during operation of the electrosurgical generator based on a first sensor signal and a second sensor signal received from the power stage or the electrosurgical instrument sensor. The first sensory feedback is determined based on the first sensor signal, and the second sensory feedback is determined based on the second sensor signal.

In aspects, the controller may receive the first sensor signal and the second sensor signal from the power stage or the electrosurgical instrument sensor. The first sensor signal and the second sensor signal may be indicative of a property selected from the group consisting tissue temperature, instrument temperature, tissue impedance, tissue permittivity, tissue permeability, tissue elasticity, force applied to electrosurgical instrument, current sourced by an electrode, voltage applied to an electrode, energy delivered by a radiator, energy reflected from a radiator, power delivered to a radiator, and power reflected from a radiator.

According to aspects, in response to receiving the first sensor signal and the second sensor signal, the controller transmits control signals to cause the audio output device to output the first sensory feedback based on the first sensor signal and to output the second sensory feedback based on the second sensor signal.

In aspects, the first sensory feedback is a first audio signal which has a first audio frequency and the second sensory feedback is a second audio signal which has a second audio frequency different from the first audio frequency. The first audio frequency may be within a first spectrum of frequencies, and the second audio frequency may be within a second spectrum of frequencies. The first spectrum of frequencies and second spectrum of frequencies may be mutually exclusive.

In accordance with aspects of the present disclosure, a method of controlling audio output of an electrosurgical generator includes transmitting electrosurgical energy from an electrosurgical generator to an electrosurgical instrument, receiving a first sensor signal and a second sensor signal in response to transmitting electrosurgical energy to the electrosurgical instrument, determining first sensory feedback and a second sensory feedback based on the first and second sensor signals, and simultaneously outputting the first sensory feedback and the second sensory feedback from an audio output device of the electrosurgical generator. Receiving the first sensor signal may include receiving a sensor signal indicative of a property selected from the group consisting of tissue temperature, instrument temperature, tissue impedance, tissue permittivity, tissue permeability, tissue elasticity, force applied to electrosurgical instrument, current sourced by an electrode, voltage applied to an electrode, energy delivered by a radiator, energy reflected from a radiator, power delivered to a radiator, and power reflected from a radiator. Receiving the second sensor signal may include receiving a different sensor signal indicative of a property selected from the group consisting of tissue temperature, instrument temperature, tissue impedance, tissue permittivity, tissue permeability, tissue elasticity, force applied to electrosurgical instrument, current sourced by an electrode, voltage applied to an electrode, energy delivered by a radiator, energy reflected from a radiator, power delivered to a radiator, and power reflected from a radiator.

In aspects, the first and second sensor signal may be received from a power stage of the electrosurgical generator or an electrosurgical instrument sensor.

According to aspects, the first sensory feedback is a first audio signal, and the second sensory feedback is a second audio signal.

In aspects, the method further includes monitoring a duration of time based on transmitting electrosurgical energy from the electrosurgical generator to the electrosurgical instrument, and determining the first or second sensory feedback based on the duration of time.

BRIEF DESCRIPTION OF THE DRAWINGS

The accompanying drawings, which are incorporated in and constitute a part of the specification, illustrate embodiments of the disclosure and, together with a general description of the disclosure given above, and the detailed description of the embodiment(s) given below, serve to explain the principles of the disclosure.

DETAILED DESCRIPTION

Figure 1:
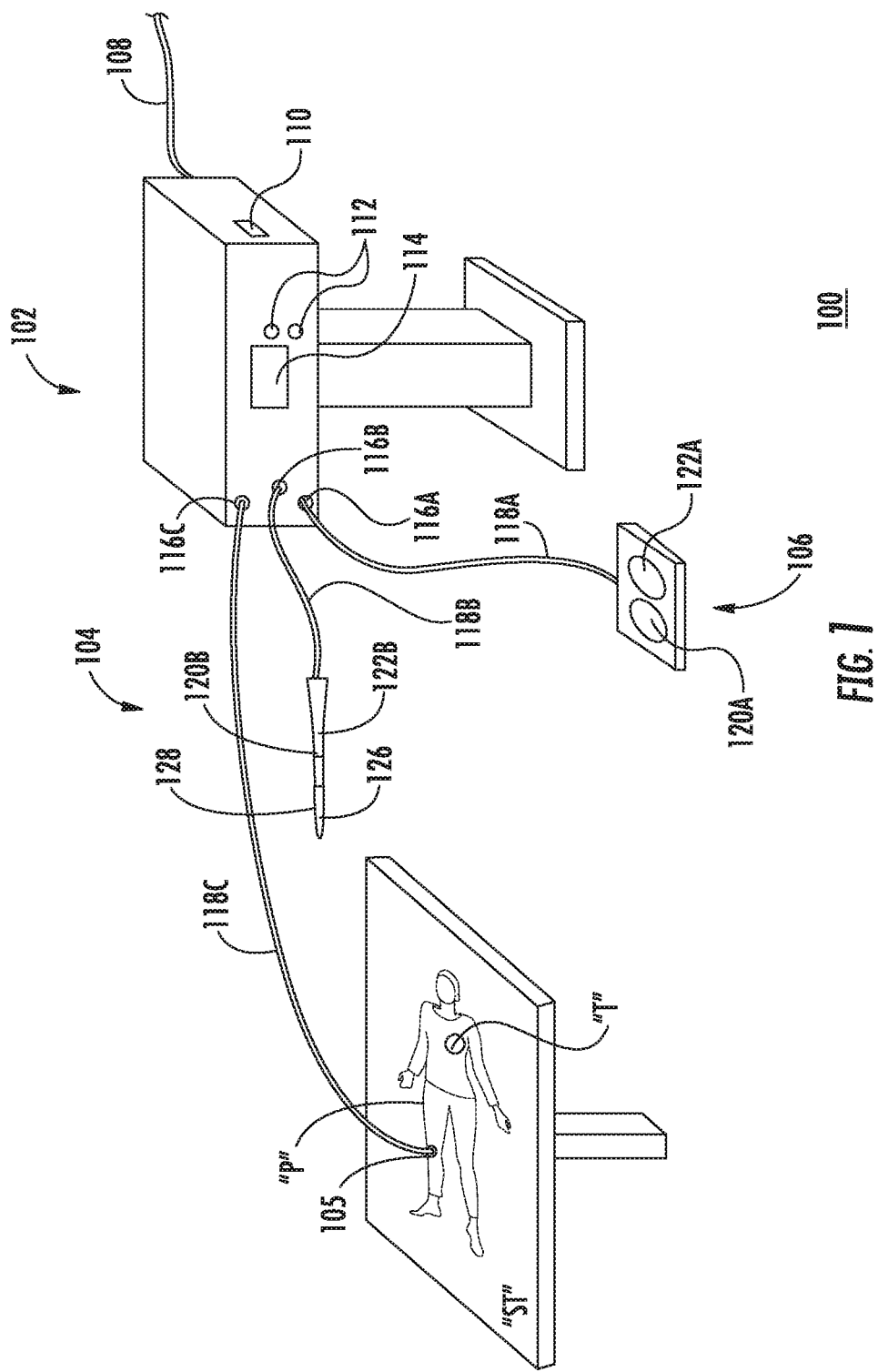
FIG. 1 is a schematic view of an electrosurgical system having an electrosurgical generator provided in accordance with an embodiment of the present disclosure.

Embodiments of the present disclosure are described in detail with reference to the drawings, in which like reference numerals may designate identical or corresponding elements in each of the several views.

During a surgical procedure, a patient is positioned on a surgical table. A generator receives electrical power from a power input and converts the electrical power into energy for use during the surgical procedure. The generator is operably coupled to an instrument and configured to transmit energy to the instrument, which delivers therapeutic energy to the patient. More particularly, when the clinician engages the instrument or an accessory, such as a foot switch or pedal, energy is transmitted to an electrode when delivering RF energy or a radiator when delivering microwave energy. The electrode or radiator is located along a distal portion of an electrosurgical or a microwave instrument, respectively, which is configured to engage target tissue of the patient during the surgical procedure. The energy is subsequently transmitted to the target tissue or tissue of the patient.

Depending on the configuration of the electrosurgical instrument or electrosurgical generator, radio frequency (RF) energy may be applied to the patient via the electrode. The electrode is in either a monopolar configuration (requiring the addition of a return electrode located along a separate portion of the patient), or bipolar configuration (requiring a second electrode in close proximity to the electrode). In the monopolar configuration, energy transmitted to the tissue returns to the electrosurgical generator via a return pad. The return pad forms a portion of a return path between the patient and the generator. Depending on the surgical procedure, energy may be produced at varying current levels, either periodically or continuously, to provide desired amounts of energy at desired rates to tissue of the patient.

As energy is transmitted from the electrosurgical generator, an audio output device transmits one or more sensory feedback indicators at either fixed or varying frequencies, such as audible signals or tones. The sensory feedback indicators may be associated with the energy applied such as, without limitation, the current level (RF ablation), the waveform of the energy applied (microwave ablation), or the duration of the application of energy. The sensory feedback indicators may alternatively be associated with properties of the tissue which are sensed by the electrosurgical instrument during the surgical procedure. The sensed tissue properties may be representative of, without limitation, tissue temperature, tissue thickness, tissue impedance, tissue permittivity, tissue permeability, tissue elasticity, and the duration of time during which the tissue receives energy. The sensory feedback may further be associated with an analysis of sensory information obtained during the surgical procedure associated with the electrosurgical generator or the electrosurgical device such as, without limitation, the temperature of the electrosurgical device, e.g., the temperature of an end effector, voltage applied to the electrode as measured by one or more voltage sensors, energy delivered by a radiator, energy reflected from a radiator, power delivered to a radiator, and power reflected from a radiator.

While sensory feedback, as described herein, refers to audible signals or tones, visual signals or cues may also be transmitted as sensory feedback. For example, symbols or lights may be illuminated on the user interface or display of a system to alert a clinician as to the state of the system or tissue being acted upon by the system. The visual signals may include a bar or other symbol displayed on the user interface. Those visual signals may be aligned with the increase or decrease of the frequency of the tones generated in accordance with aspects of the present disclosure.

As used herein, the term "clinician" refers to a doctor, nurse, or other care provider and may include support personnel. The term "distal" refers to structure that is farther from a clinician, while the term "proximal" refers to structure that is closer to the clinician. Further, directional terms such as front, rear, upper, lower, top, bottom, distal, proximal, and similar terms are used to assist in understanding the description and are not intended to limit the present disclosure.

As will be described in detail below, provided are embodiments of an example surgical system. The surgical system includes an electrosurgical generator and an electrosurgical instrument. The surgical system may also optionally include one or more electrosurgical accessories.

Referring initially to FIG. 1, one illustrative embodiment of a surgical system in accordance with the present disclosure is shown, designated generally 100. The surgical system 100 includes an electrosurgical generator 102, an electrosurgical instrument 104, and an electrosurgical accessory 106. The electrosurgical generator 104 receives electrical power from a power input 108, typically alternating current (AC), and converts the electrical power to electrosurgical energy (hereinafter "energy"). The energy may be converted to RF energy, microwave energy, etc., depending on whether the electrosurgical system is configured to apply RF energy, microwave energy, or both. The energy is then transmitted to an electrode 126 (or a microwave radiator 126 in the case of microwave ablation) of the electrosurgical instrument 104, the electrode 126 configured to transmit the electrosurgical energy to target tissue "T" of a patient "P". For purposes of clarity, unless otherwise stated any description of electrosurgical energy generation and transmission refers to the generation and transmission of RF energy. However, it will be appreciated that the systems and methods disclosed are generally applicable to both RF and microwave ablation configurations.

The electrosurgical generator 102 includes a power switch 110, one or more clinician inputs 112, a display 114, and electrosurgical I/O ports 116A, 116B, 116C. When manipulated, the power switch 110 transitions the electrosurgical generator between an active state and an off state. In the off state the electrosurgical generator 102 does not respond to clinician input and prevents the transmission of electrosurgical energy to the electrosurgical device 104. In the active state, the electrosurgical generator 102 is configured to provide energy to the electrosurgical device 104 when either the electrosurgical device 104 or the electrosurgical accessory 106 are engaged by the clinician. The electrosurgical generator 102 may also receive input from the clinician inputs 112, thereby modulating parameters associated with energy application such as the current level (RF) or the waveform of the energy applied. As monopolar energy is applied, the electrosurgical generator 102 additionally receives energy from an energy return pad 105 coupled to the patient "P" and operably coupled to the electrosurgical generator 102. Alternatively, as bipolar energy is applied, the electrosurgical generator 102 receives energy from a return electrode (not shown) located on the electrosurgical instrument. The internal components and circuitry of the electrosurgical generator 102 will later be described in greater detail.

The display 114 includes an electroluminescent panel configured to communicate information to the clinician during operation of the electrosurgical generator 102, such as the mode of energy application selected (e.g., a cut mode or a coagulation mode), the level of the current applied (e.g., amperes, or as a percent measured by the energy supplied relative to the total possible energy output of the electrosurgical generator 102 or the electrosurgical instrument 106), and energy delivery type (e.g., monopolar energy delivery, bipolar energy delivery). The application mode, and current applied may be manipulated (increased, decreased, or changed) by engaging the clinician inputs 112. The electrosurgical generator 102 further includes an audio output device 214 (FIG. 2) contained therein. The audio output device 214 may include one or more suitable speakers for providing an audible signal.

The electrosurgical generator 102 may output energy at various current levels (RF ablation) and in various waveforms (microwave ablation) depending on the surgical procedure performed (e.g., without limitation, pulsing energy, constant energy, and combinations thereof). For example, while cutting target tissue "T" energy may be continuously transmitted from the electrosurgical generator 102; for more precise cutting energy may be transmitted in pulses; and for coagulation energy may be transmitted at a lower frequency relative to the frequency used to cut the target tissue "T".

The electrosurgical I/O ports 116A, 116B, 116C include an electrosurgical accessory port 116A, an electrosurgical instrument port 116B, and a monopolar return port 116C, the electrosurgical I/O ports 116A, 116B, 116C are further configured to receive connection wires 118A, 118B, 118C, respectively. The connection wires 118A, 118B, 118C operably couple the electrosurgical accessory 106, the electrosurgical instrument 104, and the energy return pad 105, respectively, to the electrosurgical generator 102.

Electrosurgical accessory port 116A is configured to couple to an electrosurgical accessory 106 which includes a first energy pedal 120A and a second energy pedal 122A. When engaged by the clinician, the first energy pedal 120A causes energy to be applied for cutting tissue "T". Alternatively, when engaged, the second energy pedal 122A causes energy to be applied for blood coagulation. Similar to the electrosurgical accessory 106, the electrosurgical instrument 104 includes a first energy button 120B and a second energy button 122B. When engaged by the clinician, the first energy button 120B causes energy to be applied for cutting tissue "T". Alternatively, when engaged, the second energy button 122B causes energy to be applied for blood coagulation.

The electrosurgical instrument port 116B is configured to couple to the electrosurgical instrument 104, for operable connection to the electrode 126 and one or more sensors 128 located thereon. The electrosurgical instrument port 116B and/or the electrosurgical generator is further configured to receive sensor signals from the one or more sensors 128 indicative of, without limitation, tissue width, tissue temperature, tissue impedance, tissue permittivity, tissue permeability, and tissue elasticity, of the target tissue "T" of patient "P". The electrosurgical instrument port 116b is further configured to receive sensor signals from the one or more sensors 128 indicative of, without limitation, the temperature of the electrosurgical instrument 104, forces applied to or by the electrosurgical instrument 104, current sourced by or flowing through an electrode 126 disposed on the electrosurgical instrument 104, voltage applied to the electrode 126, electrode temperature, or any combination of these sensor signals. The microwave ablation systems according to the present disclosure may be further configured to receive sensor signals from one or more sensors indicative of, without limitation, the temperature of the microwave instrument, forces applied to or by the microwave instrument, energy delivered by a radiator of the microwave instrument, energy reflected from the radiator, power delivered to the radiator, power reflected from the radiator, radiator temperature, or any combination of these sensor signals.

Figure 2:
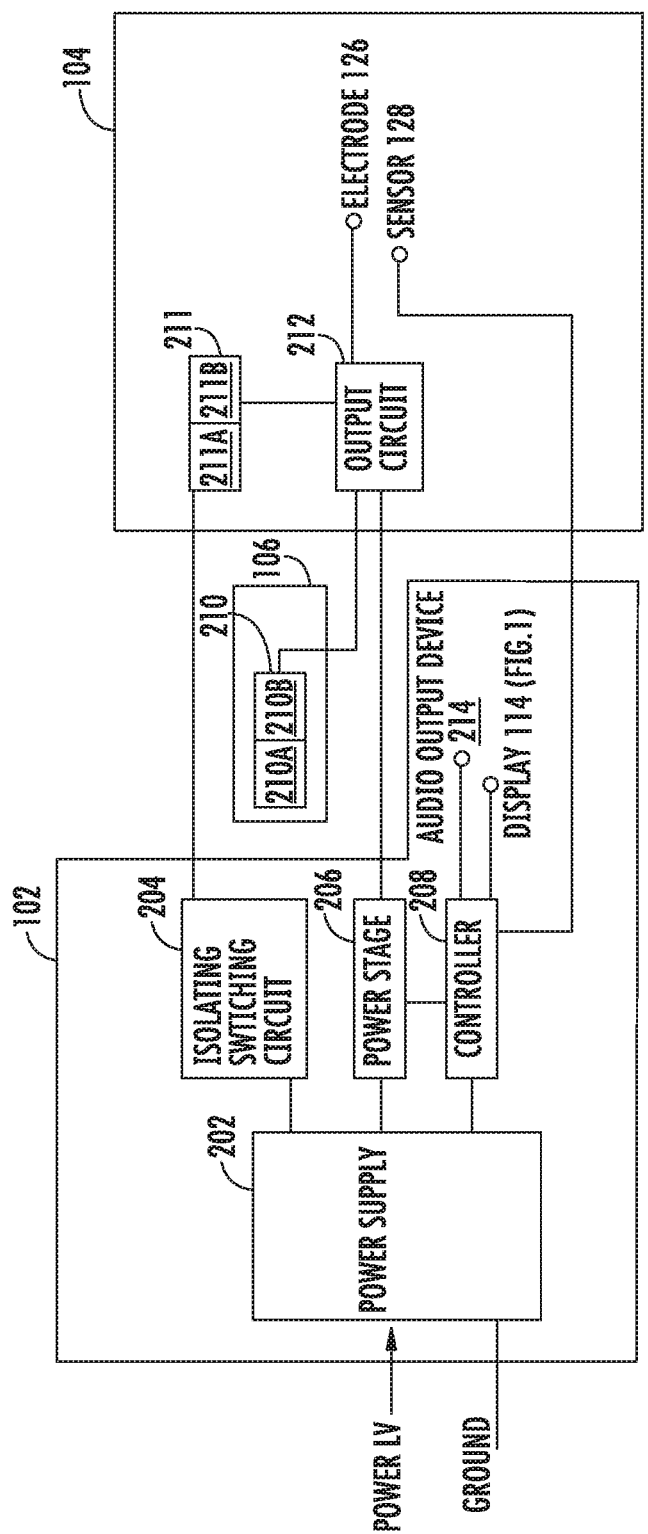
FIG. 2 is a schematic view of control system for controlling the electrosurgical components of FIG. 1.

As the electrosurgical instrument port 116B receives sensor signals, the received sensor signals are transmitted to the controller 208 (FIG. 2). When monopolar energy is applied to tissue "T", the energy applied by the electrosurgical instrument 104 passes through the patient "P" and returns to the electrosurgical generator 102 via the energy return pad 105. When bipolar energy is applied, the energy is returned to the electrosurgical port 116B via a second electrode (not shown) located on the electrosurgical instrument 104.

Referring to FIG. 2, a control system is illustrated, including a power supply 202, an isolating switching circuit 204, a power stage 206, a control circuit or controller 208, first and second switch circuits 210, 211, an output circuit 212, and an audio output device 214, the control system designated generally 200. The power supply 202 generally receives an alternating current (A/C) at an input port. The power supply 202 is further coupled to an electric ground. In use, the power supply 202 provides power to the isolating switching circuit 204, the power stage 206, and the controller 208.

The isolating switching circuit 204 supplies an electric current to the first and second energy pedal 120A, 122A as well as the first and second energy buttons 120B, 122B. The first switch circuit 210 includes first and second switches 210A, 210B which are in the closed position when first or second energy pedal 120A, 122A are engaged by the clinician, respectively. Likewise, the second switch circuit 211 includes first and second switches 211A, 211B which are in the closed position when the first or second energy button 120B, 122B are engaged by the clinician, respectively. While in the closed position, the first or second switch 210, 211 cause the output circuit 212 to transmit energy to the electrosurgical instrument 104.

The power stage 206 receives an electrical current from the power supply 202 and converts the electrical energy to electrosurgical energy or energy for transmission to the output circuit 212. Based on control signals received from the controller 208, the power stage 206 may modulate the energy transmitted by pulsing, pausing, increasing or decreasing the current, or otherwise modulating the energy transmitted to the output circuit 212. More particularly, the controller 208 may send control signals to cause the power stage 206 to transmit energy at varying current levels and/or at varying intervals based on input received by the clinician and/or tissue properties sensed by the one or more sensors 128 located on the electrosurgical instrument 104.

The controller 208 includes a processor and memory coupled to the processor (not shown). The processor is configured to execute instructions stored in the memory and transmit control signals to the power stage 206 to control the transmission of energy from the power stage 206 to the output circuit 212, thereby modulating energy transmitted to the electrosurgical instrument 104 (FIG. 1) as desired in response to clinician input. For example, the controller 208 may transmit control signals to cause the power stage 206 to continuously transmit energy at a first current level to the output circuit 212 for delivery to tissue "T" as the clinician engages the first energy button 122A. Simultaneously, the controller 208 may transmit control signals to cause the power stage 206 to transmit energy at a second current level or at a particular interval to the output circuit 212 for when the clinician engages the second energy button 122B.

The output circuit 212 is configured to receive energy from the electrosurgical tool 104, the electrosurgical accessory 106, and the power stage 206. As the clinician engages the first or second energy pedal 120A, 120B, or first or second energy button 120B, 122B, the first or second energy switch 211, 212 transmits a control signal to the output circuit 212 to transmit energy to the electrode 126. More particularly, when the first energy pedal 120A or the first energy button 122A are engaged, the output circuit 212 receives a signal to apply energy to cut tissue "T". Alternatively, when the second energy pedal 120B or the second energy button 122B are engaged, the output circuit 212 receives a signal to apply energy to cause coagulation. In response to receiving signals from the first or second energy switch 211, 212, the output circuit 212 permits transfer of energy from the power stage 206 to the electrode 126.

The sensor 128 of the electrosurgical instrument 104 (FIG. 1), the display 114 (FIG. 1), and an audio output device 214 are operably coupled to the controller 208. The sensor 128 transmits sensor signals to the controller 208 based on sensing one or more properties of the tissue "T" or the electrosurgical instrument 104. As noted above, sensed properties may include, without limitation, tissue temperature, tissue width, tissue impedance, and temperature of the electrosurgical instrument 104. The display 114 outputs information via the electroluminescent panel for review by the clinician. An audio output device 214 is operably coupled to the controller 208 and receives both control signals and power therefrom. More particularly, the audio output device 214 is configured to output audio at varying frequencies, and at varying intervals, based on control signals received from the controller 208. Audio output generation will be described in greater detail below.

For a detailed description of electrosurgical systems, reference may be made to U.S. Pat. Nos. 8,920,421, 8,221, 418, and 7,364,578, the entire disclosures of which are hereby incorporated by reference.

Figure 3:
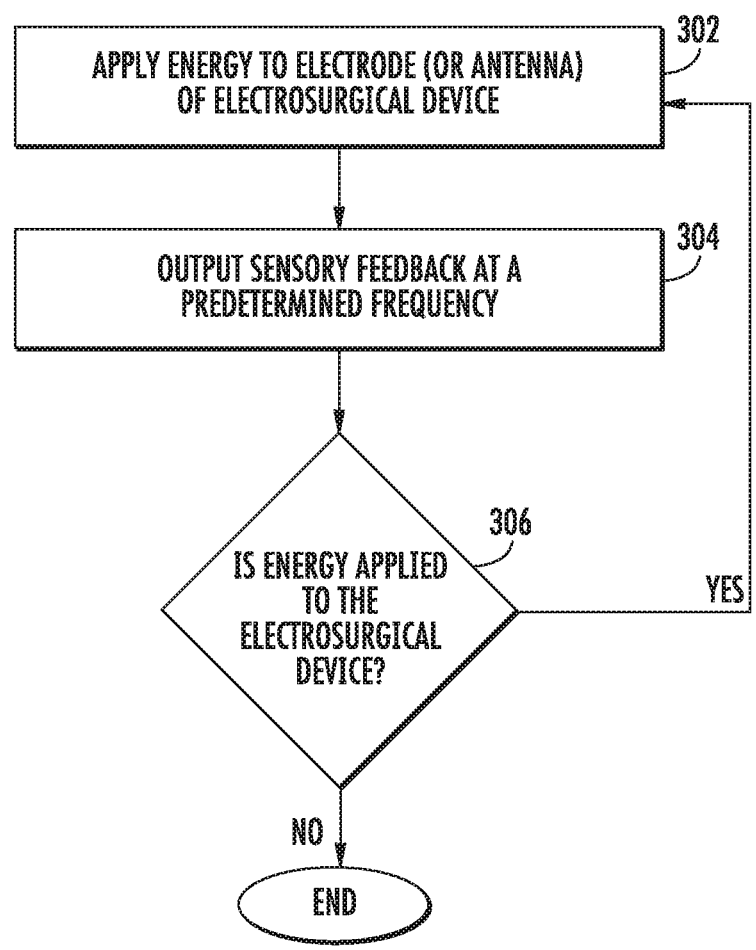
FIG. 3 is a flow diagram illustrating a method of providing audio feedback in response to clinician engagement of tissue with an electrosurgical device.

Referring to FIG. 3, a flow diagram of a prior art electrosurgical sound generation process 300 (hereinafter "process 300") for generating audio signals based energy generation is described with reference to the electrosurgical system 100 of FIG. 1 and control system 200 of FIG. 2. During the process 300, the clinician engages the first or second energy pedal 120A, 120B, or the first or second energy button 120B, 122B, thereby causing the electrode 126 of the electrosurgical device 104 to receive energy (block 302). In response to engagement of the first or second energy pedal 120A, 120B, or the first or second energy button 120B, 122B, the audio output device 214 outputs an audible signal at a predetermined frequency (block 304). The audible signal is transmitted at a predetermined frequency to indicate to the clinician the electrode 126 is energized. While energy continues to be applied (block 306), the process 300 continues to cause the audio output device 214 to output the audio signal (block 304). Alternatively, when it is determined that energy is no longer applied to the electrode 126, the process 300 ends.

Figure 4:
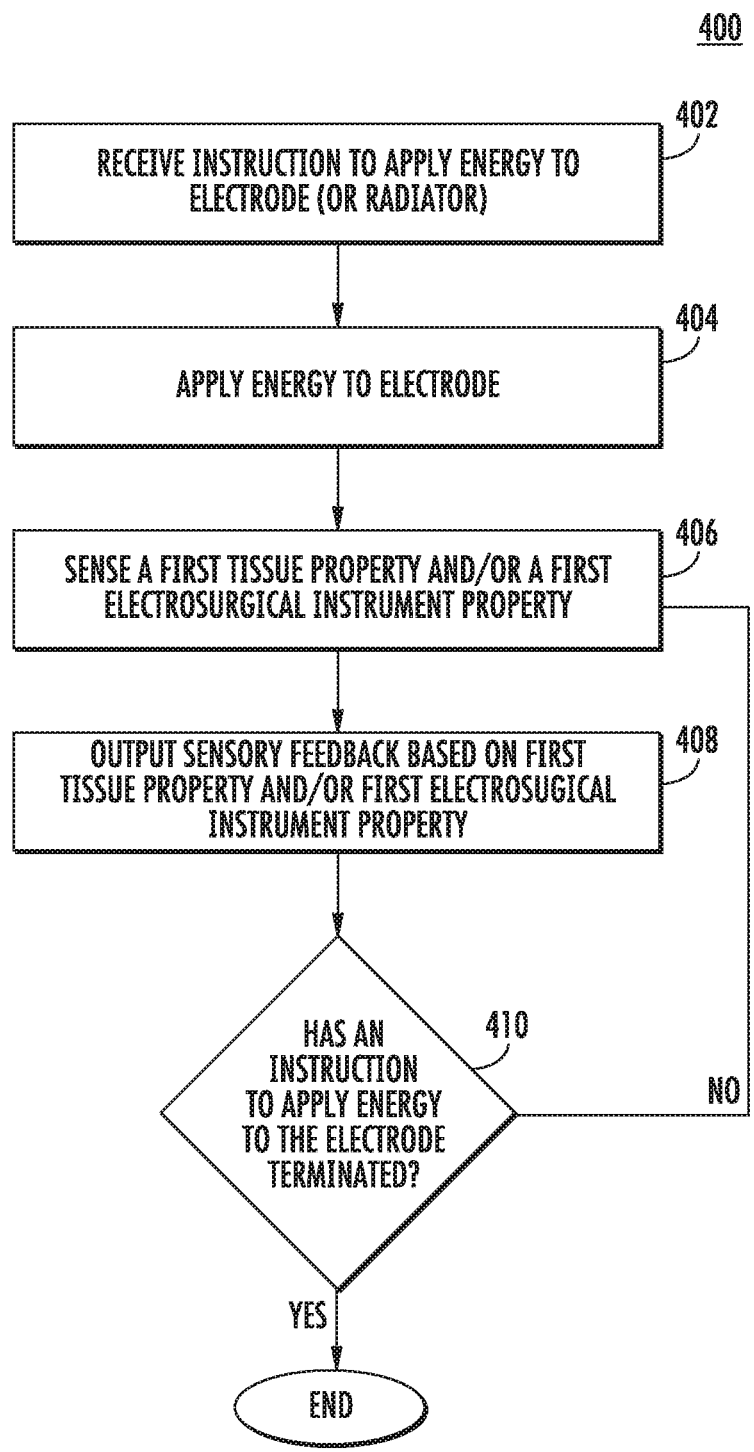
FIG. 4 is a flow diagram of an electrosurgical sound generation process for generating sensory feedback in response to clinician engagement of tissue with an electrosurgical instrument.

Referring now to FIG. 4, a flow diagram of an electrosurgical sound generation process 400 (hereinafter "process 400") for generating sensory feedback based on clinician engagement of an electrosurgical instrument 104 is described. Initially, the clinician positions the electrosurgical instrument 104 such that the electrode is in contact with tissue "T" of the patient "P". The clinician engages the first or second energy pedal 120A, 120B of the electrosurgical accessory 106, or the first or second energy button 120B, 122B of the electrosurgical device 104 while the electrosurgical generator 102 in an active mode. In response to clinician engagement of the first or second energy pedal 120A, 120B, or the first or second energy button 120B, 122B, the output circuit 212 transmits signal energy to the electrode 126 located on the electrosurgical instrument 104 (block 402), causing the output circuit 212 to transmit energy to the electrode 126 (block 404). The at least one sensor 128 senses or measures a first tissue property or a first electrosurgical instrument property, and converts the first tissue property or the first electrosurgical instrument property into sensor data to be transmitted to the controller 208

(block 406). The first tissue property may include, without limitation, tissue temperature, tissue impedance, tissue permittivity, tissue permeability, tissue elasticity, and force applied by the electrosurgical instrument to tissue. Additionally, or alternatively, the first instrument property may include, without limitation, the temperature of the electrosurgical instrument 104 or a microwave instrument, force applied to the electrosurgical instrument 104 or the microwave instrument, the position of one or more jaw members (not shown) located on the electrosurgical instrument 104, energy delivered by the electrode 126 of the electrosurgical instrument 104 (or radiator of the microwave instrument), energy reflected from the radiator, power delivered to the radiator, and power reflected from the radiator. To determine tissue thickness, one or more encoders (not explicitly shown) may be disposed about the one or more jaw members of the electrosurgical instrument, the encoders configured to transmit sensor signals to the controller 208 indicative of the position of the jaw members relative to each other. The controller 208 subsequently calculates a thickness of the portion of the tissue being acted upon by the electrosurgical instrument 104 based on the position of the jaw members relative to each other.

Based on the sensor data received from the at least one sensor 128, the controller 208 sends control signals to the audio output device 214 to output sensory feedback (block 408). The process of applying energy (block 404), sensing the first tissue property (block 406), and outputting sensory feedback (block 408) may be repeated to provide continuous sensory feedback in response to sensing the first tissue property. The frequency or amplitude of the sensory feedback may be modulated or modified after each iteration of block 408 in response to changes in the sensed first tissue property (block 406). The frequency at which the sensory feedback is output may be further be a function of the sensed first tissue property or the first sensed instrument property. Alternatively, the sensory feedback may be output at predetermined frequencies within a frequency spectrum associated with temperature or impedance ranges (sensory feedback may be output to indicate a normal operating tissue temperature or a normal operating electrosurgical instrument temperature, etc.).

The sensory feedback, which includes audible signals or tones, may increase or decrease in frequency within a frequency spectrum in response to changes to the electrosurgical instrument 104 or tissue "T" of patient "P" during a surgical procedure. In addition or in the alternative, the sensory feedback may increase or decrease in amplitude or volume. As the frequency of the tone or tones increases, clinicians may be alerted to surgical procedure-specific information including the completion of a particular operation (i.e., ablation of a certain region along the tissue "T" of patient "P"), or a change in reaction of the target tissue "T" during a procedure (e.g., an ablation zone is slowing in growth). Similarly, an increase in frequency of a tone within a frequency spectrum may indicate or alert clinicians to the overheating of the electrosurgical device 104, as measured by the one or more sensor 128, or that tissue is desiccated or otherwise dehydrated as a result of the surgical procedure.

For surgical procedures which include continuous repositioning or advance of the electrode 126 relative to the tissue "T" of the patient, such as "track" ablation where the ablation procedure proceeds along a "track" or predefined trajectory through the target tissue "T", the tone may be pulsed (e.g., a beeping tone) at a predetermined tempo or rate to indicate normal operation of the electrosurgical device 104.

For example, during track ablation or ablation along a predetermined trajectory, the tone may be pulsed at varying or predetermined rates depending on the rate at which the electrode 126 advances through the target tissue "T". When the rate of advance of the electrode 126 is less than a predetermined rate the tones may be pulsed at a first rate to indicate that the rate of advance of the electrode 126 should be increased. Similarly, when the rate of advance of the electrode 126 is greater than the predetermined rate, the tones may be pulsed at a second rate to indicate that the rate of advance should be decreased.

Figure 6A:
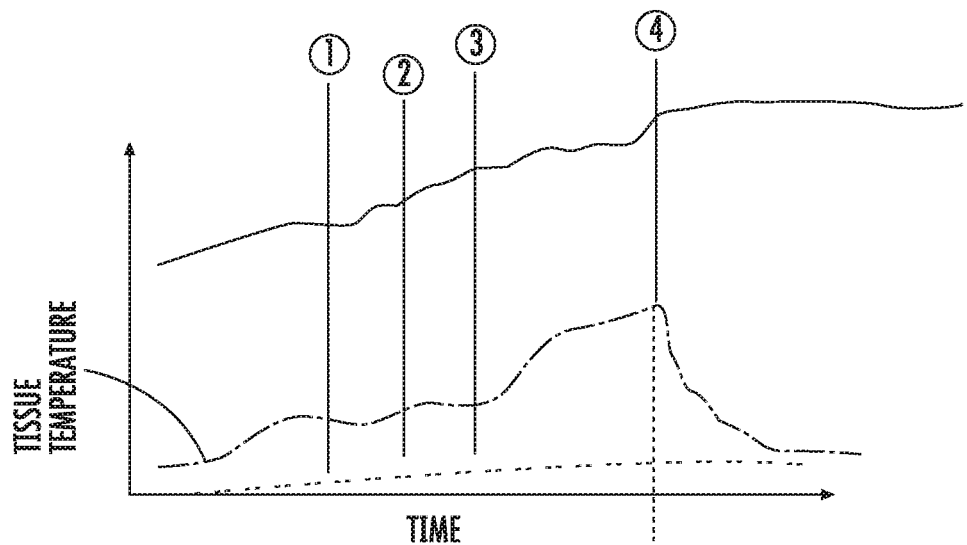
FIGS. 6A and 6B are diagrams of sensory feedback generated relative to sensing a property of an electrosurgical instrument or a property of tissue.
Figure 6B:
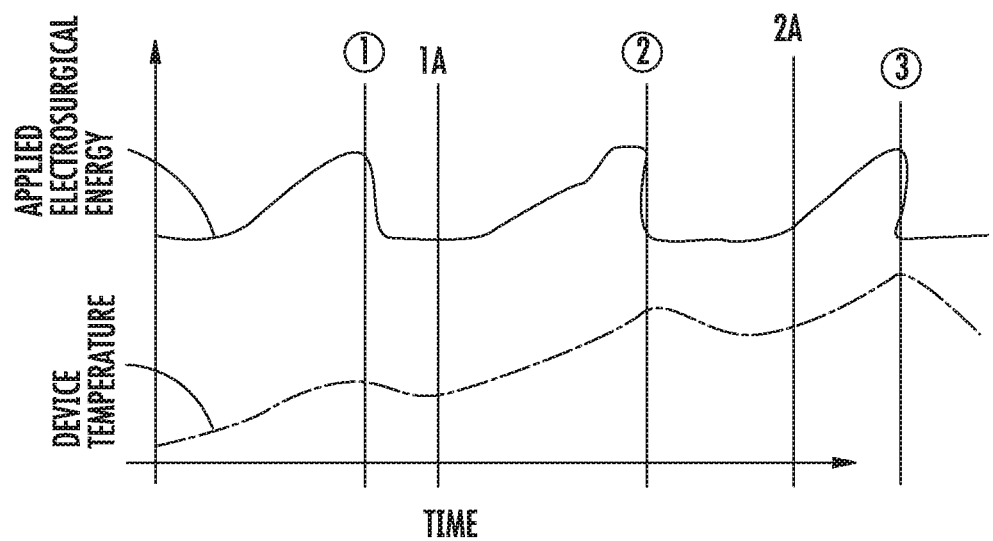

The frequency of the tones or the tempo of the tone pulses may increase to indicate to the clinician that the electrosurgical device 104 should be advanced to another location during the surgical procedure based on sensor signals received during the surgical procedure. Similarly, the tempo of the tone pulses may be increased or decreased to signal to the clinician that movement of the electrode 126 relative to the tissue "T" should be hastened or delayed when the sensed tissue properties indicate that a certain operation on the target tissue is complete in that particular region. For example, when retracting an electrode 126 through target tissue "T", to encourage retraction at a constant rate per unit of time, a repeating rising tone may be provided to indicate a rate of retraction (e.g., for each rising tone over a five second interval, retraction of the electrode 126 by 10 mm is encouraged). Examples of sensory outputs or tones generated in response to sensing the first tissue property is illustrated in FIGS. 6A-6B, which are described in greater detail below.

Figure 5:
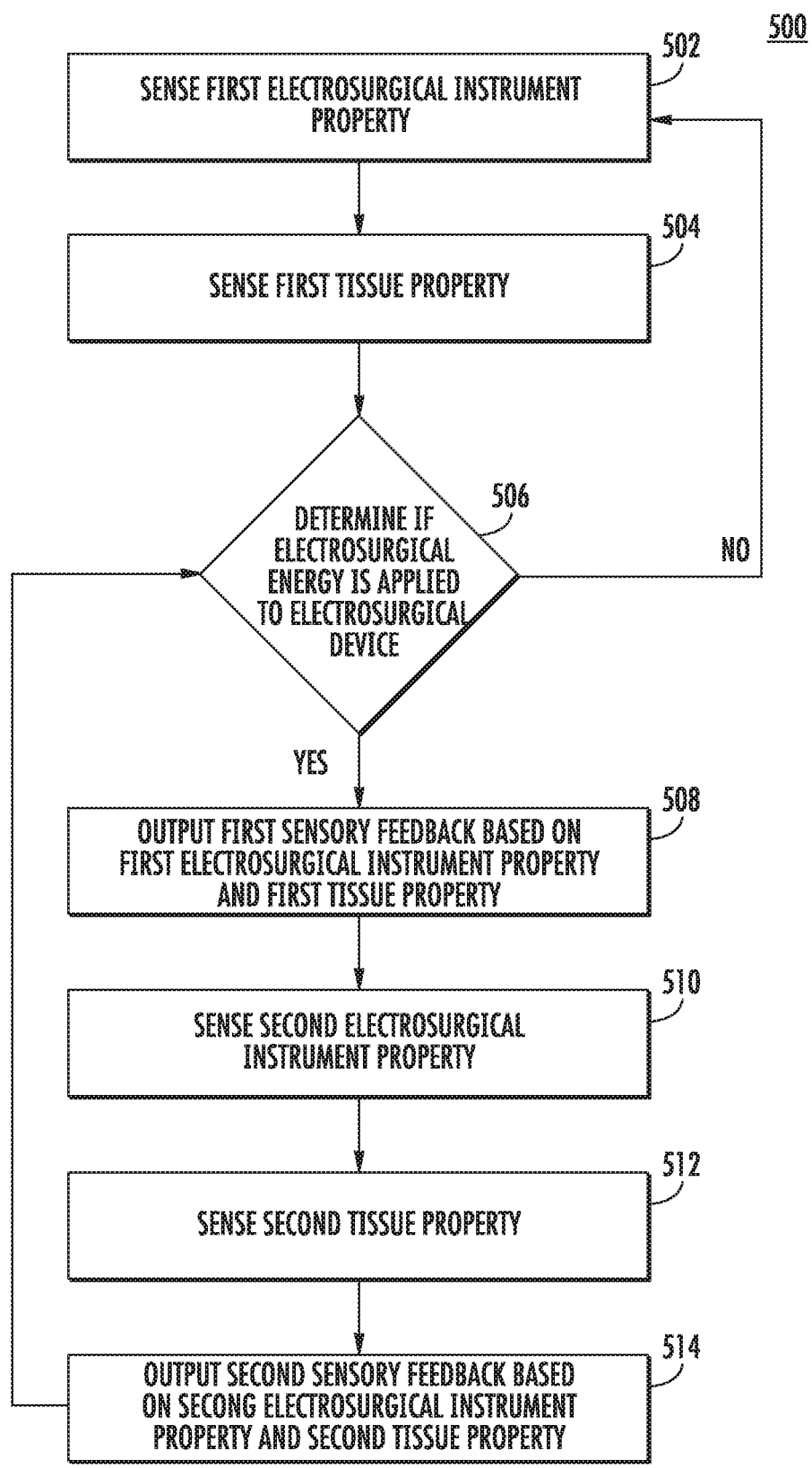
FIG. 5 is a flow diagram of a second electrosurgical sound generation process for generating sensory feedback in response to clinician engagement of tissue with an electrosurgical instrument.

Referring now to FIG. 5, a flow diagram of an electrosurgical sound generation process 500 (hereinafter "process 500") for generating sensory feedback in response to clinician engagement of an electrosurgical instrument 104 is described. Initially, the controller 208 receives sensor data in response to the one or more sensors 128 of the electrosurgical device 104 sensing a first electrosurgical instrument property (block 502) and a first tissue property (block 504). When the controller 208 determines energy is not being applied to the electrode 126 (block 506), the controller 208 continues to receive sensor data from the one or more sensors 128 to sense the first electrosurgical instrument property (block 502) and the first tissue property (block 504).

When the controller 208 determines that energy is applied to the electrode 126 (block 506) the controller 208 causes the audio output device 214 to output first sensory feedback based on the sensed first electrosurgical instrument property and the first sensed tissue property (block 508). The first sensory feedback includes a first audio signal and a second audio signal generated at a first frequency and a second frequency, respectively. The first frequency may fall within a first range or spectrum and the second frequency may fall within a second range or spectrum. The first and second spectrums may be mutually exclusive or may overlap.

The controller 208 then receives a second electrosurgical instrument property (block 510) and a second tissue property (block 512) from the at least one sensor 128 and outputs a second sensory feedback (block 514). The second sensory feedback includes a third audio signal and a fourth audio signal having a third frequency and a fourth frequency within the first and second spectrum, respectively. The third and fourth frequencies may be generated based on the sensed second electrosurgical instrument property and the sensed second tissue property. Alternatively, the third and fourth frequencies may be generated based on a measured deviation between the first and second electrosurgical instrument properties, and the sensed first and second tissue properties, respectively.

As described above, the controller 208 may sense a first electrosurgical instrument property, a second electrosurgical instrument property, a first tissue property, or a second tissue property, and in response to sensing the first and second properties, transmit control signals to the audio output device 214 to output a first sensory feedback and a second sensory feedback. While operations of the controller 208 are described with respect to individual or distinct sensory feedback signals or tones, the frequencies of multiple tones which fall within one or more spectrums may be transmitted by the audio output device 214 to the clinician to signal one or more sensed properties. For example, a first tone and a second tone may be output simultaneously to indicate a first electrosurgical instrument property and a first tissue property. Output of the first and second tones enable the clinician to identify, independently, the state of the surgical system 100 as well as the state of tissue "T" of the patient "P" acted upon by the surgical system 100.

Described herein are different scenarios during which the controller 208 may cause the audio output device 214 to transmit varying sensory feedback based on sensing first and/or second electrosurgical instrument(s) and tissue properties. Such scenarios are provided only for illustrative purposes and are not intended to limit the scope of the present disclosure.

When either the sensed electrosurgical instrument property or the sensed tissue property is determined to be outside of a normal range, the controller 208 may cause the audio output device 214 to transmit a third audio signal indicative of an error or warning. For example, when the at least one sensor 128 senses a temperature of the electrosurgical instrument 104 greater than or less than an acceptable operating temperature for the particular procedure, the controller 208 may cause the audio output device 214 to transmit a continuous audio signal or series of audio signals at a higher or lower frequency than frequencies produced during normal operation of the electrosurgical device 104. Likewise, when the at least one sensor 128 senses a temperature of the tissue "T" greater or less than a preferred tissue temperature for the surgical procedure, the controller 208 may cause the audio output device 214 to transmit a continuous audio signal or series of audio signals at a higher or lower frequency than frequencies produced during normal operation of the electrosurgical instrument 104.

In the case of microwave ablation, the surgical system 100 may include a network analyzer (not shown) that measures one or more properties (e.g., power, distortion, and/or harmonics) of transmitted and/or reflected microwave signals propagating through a transmission line coupled between the microwave generator and the microwave radiator during surgical procedures. The network analyzer, which may include a spectrum analyzer, transmits signals to the controller 208 in response to measuring one or more properties of the transmitted and reflected microwave signals. A predetermined threshold indicative of normal operation of the microwave system may be set by the manufacturer or by the clinician. When a measured property of the reflected or transmitted microwave signal is greater than the predetermined threshold, which is preset in the controller 208 by the manufacturer or by the clinician, the controller 208 transmits control signals to the audio device 214, which causes the audio device 214 to output audible sound waves, e.g., one or more tones, indicative of the measured property, e.g., power of the reflected microwave signal, is greater than a predetermined threshold, thereby alerting the clinician to a possible abnormality or condition that requires adjustment of a property of the microwave signal.

Alternatively, in the case of electrosurgery (or RF ablation), the surgical system 100 may include one or more electrical sensors (not shown) disposed along circuitry located within the generator (FIG. 2), on the connection wires 118B, 118C, on the electrosurgical instrument 104, at the electrode 126, at the return pad 105, or any combination thereof. The electrical sensors transmit sensor signals to the controller 208 in response to measuring, for example, the voltage and/or current relative to the components to which the electrical sensors are attached. The controller 208 then analyzes the voltage and/or current and compares the voltage and/or current measurements to predetermined values indicative of normal operation.

Alternatively, the voltage and/or current measurements of each electrical sensor may be compared to or analyzed with respect to each other, either periodically or continuously. When electrical deviations greater than predetermined thresholds are measured, the controller 208 determines that an abnormal condition exists between the various components operably coupled between the electrical sensors. In response to detecting electrical deviations greater than the predetermined value, or electrical deviations between components greater than the predetermined threshold, the controller 208 transmits control signals to the audio device 214. The control signals cause the audio device 214 to generate audible sounds waves or multiple audible sound waves, to alert the clinician to electrical deviations or mismatches.

With continued reference to FIG. 5, sensing the first tissue property (block 504) or sensing the second tissue property (block 506) may include sensing the position of the electrosurgical device 104 or microwave instrument, or the position of the electrode 126 or radiator, relative to the anatomical feature being acted upon or treated. To achieve this, the controller 208 may refer to a navigation plan stored in memory. The navigation plan may include a representation of one or more anatomical features of the patient "P" scanned prior to the surgical procedure. As the clinician advances the electrode 126 or radiator through the target tissue "T" of the patient "P", the controller 200 may receive sensor signals from the electrosurgical device 104 or microwave instrument indicative of the position and/or orientation of the electrode 126 or radiator relative to the patient "P". The position and/or orientation may then be matched to the navigation plan associated with the patient "P" and compared to the sensed position and/or orientation of the electrode 126 or radiator (this process is often referred to as registration). As the electrode 126 advances toward or through target tissue "T", the controller 208 may calculate the distance of the electrode 126 to the target tissue "T". In response to calculating the distance, the controller 208 may transmit control signals to the audio output device 214 to output tones (blocks 508, 510) to indicate the position of the electrode 126 or radiator.

In embodiments, tones may be output by the audio output device 214 before the controller 208 determines that energy is applied via the electrosurgical device 104 or microwave instrument. The delivery of tones may occur in response to sensing the first electrosurgical instrument property (block 502). A detailed description of registration and planning of the navigation of a surgical device traveling through a patient may be found in commonly-owned U.S. Patent Application No. 2016/0000302, filed Jun. 29, 2015, entitled "SYSTEM AND METHOD FOR NAVIGATING WITHIN THE LUNG", as well as U.S. Patent Application Publication No. 2016/0317229, filed on Apr. 15, 2016, entitled "METHODS FOR MICROWAVE ABLATION PLANNING AND PROCEDURE", the contents each of which are hereby incorporated by reference in their entirety.

In some embodiments, the tones output by the audio output device 214 may be modulated as the electrosurgical instrument 104 moves toward the target tissue "T". For example, the clinician initially may insert an electrosurgical instrument 104 or microwave instrument into the body of the patient "P" either percutaneously or through one or more cavities such as bronchial tubes of the patient "P". As the electrosurgical instrument 104 moves toward the target tissue "T" of the patient "P", the controller 208 registers the position and orientation of the electrosurgical instrument 104, and calculates a distance between the electrode 126 of the electrosurgical instrument 104 and the target tissue "T". As the electrode 126 or radiator comes within a predetermined distance from the target tissue "T" (e.g., two inches), the controller 208 may transmit control signals to cause the audio output device 214 to output sensory feedback or tones indicative of the distance between the electrode 126 or radiator and the target tissue "T".

In embodiments, tones may be generated at any point before the electrosurgical instrument 104 makes contact with the target tissue "T" of the patient "P". The frequency of the tones may subsequently increase in frequency or the pulsed tones may subsequently increase in tempo as the distance between the electrosurgical instrument 104 and the target tissue "T" decreases. As a result of the modulation of the tempo and/or frequency, the clinician may more accurately approximate the location of the electrosurgical instrument 104 during the surgical procedure.

FIGS. 6A and 6B illustrate electrosurgical instrument measurements and tissue measurements measured by the one or more sensors 128 positioned about the target tissue "T" of the patient "P" during a surgical procedure.

In FIG. 6A, tissue impedance and tissue temperature are measured over time while operation of the surgical system 100 occurs during a surgical procedure. Initially, as energy is applied to the electrode 126 by the electrosurgical generator 102, both tissue temperature and tissue impedance increase as a result of the transfer of energy to the tissue "T". The controller 208 may measure the duration of time during which energy is transferred to the tissue and cause a sensory output to be transmitted from the audio output device 214. For example, at time T=1, the controller 208 transmits a signal to the clinician after determining the ablation of the tissue "T" should be paused to allow for tissue rehydration and/or to prevent or reduce the chance of a fluid phase transition. After pausing, the clinician may continue to cause the electrode 126 to apply energy to the target tissue "T", and this cycle of notifying the clinician to pause for tissue rehydration may repeat at times T=2, and T=3. At time T=4, the controller 208 determines the tissue "T" has been cut based on the measured tissue impedance received from the one or more sensors 128 and transmits sensory feedback to the clinician. More particularly, once the impedance fails to increase and/or the impedance exceeds a predetermined threshold impedance, the controller 208 determines the tissue "T" is cut. In response to determining the tissue "T" is cut at time T4, a signal is output by the audio output device 214 within a predetermined frequency indicative of the tissue "T" being cut, or the predetermined threshold impedance being achieved. In response, the clinician stops applying energy to the tissue, thereby causing the sensed tissue temperature to decrease.

FIG. 6B illustrates electrosurgical energy (i.e., energy applied via the electrosurgical instrument 104 to the target tissue "T" of the patient "P") (FIG. 1) and sensed device temperatures over time. During the course of a surgical procedure, as electrosurgical energy is applied to target tissue "T" via the electrode 126 of the electrosurgical instrument 104 (FIG. 1), the temperature of the electrode 126 increases. In order to prevent overheating of the electrode 126, the audio output device 214 (FIG. 2) outputs a first tone at time T=1 indicating that the electrosurgical device 104 is about to overheat. The clinician, in response to hearing the tone, may cause the electrosurgical instrument 104 to stop delivering electrosurgical energy to the target tissue "T".

At time T=1A, once the controller 208 (FIG. 2) determines that the electrode 126 has cooled to a temperature at which the electrode 126 can continue to operate effectively, the audio output device 214 outputs a second tone to indicate to the clinician that the electrosurgical instrument 104 can be re-energized. This process is repeated again at times T=2 and T=2A, with the device transmitting the first tone and the second tone at times T=2 and T=2A, respectively. This process may be further repeated, with the audio output device 214 transmitting the first and second tone, to alert the clinician that she can continue use of the electrosurgical instrument 104.

It is contemplated that, as the controller 208 monitors the one or more tissue properties, the controller 208 may determine that the impedance may not be rising at a rate desired during the surgical procedure (e.g., the clinician may have set the power level at the generator too low). In response to determining that the duration necessary to achieve a certain tissue property is greater than a desired duration, the controller 208 may send control signals to cause the audio output device 214 to output sensory feedback to indicate to the clinician to increase the power setting at the electrosurgical generator 102. Likewise, the controller 208 may determine, in response to sensing one or more tissue properties, that the power setting should be increased to accelerate the ablation process. In response to determining that power should be increased the controller 208 may send control signals to cause the audio output device 214 to output sensory feedback to indicate to the clinician to increase the power setting at the electrosurgical generator 102.

Additionally, the controller 208 may receive sensor feedback from the one or more sensors 128, and may further measure an amount of time which ablation of the target tissue "T" has occurred. When the period of time exceeds a desired or predetermined time period for ablating the tissue "T", the controller 208 may transmit control signals to the audio output device 214 to output sensory feedback to indicate to the clinician that the electrode 126 should be moved to engage a different portion of the tissue "T". Alternatively, the controller 208 may determine that further ablation is desirable, and may cause the audio output device 214 to output sensory feedback to indicate to the clinician to continue ablating the target tissue. In addition to determining desired ablation times based on the duration which energy is applied to target tissue "T", the controller 208 may send signals to indicate to the clinician that fluids associated with the target tissue "T" may be approaching a phase transition.

It will be understood that various modifications may be made to the embodiments of the presently disclosed surgical system 100. Therefore, the above description should not be construed as limiting, but merely as exemplifications of embodiments. Those skilled in the art will envision other modifications within the scope and spirit of the present disclosure. For example, while sensory feedback is described with respect to electrosurgical and microwave systems, it is envisioned that the sensory feedback may be applied to other types of surgical systems including ultrasonic surgical devices. Additionally, while audio output is described with regard to outputting one or more frequencies from an audio output device, one skilled in the art will be able to envision outputting audio files, or other similar predetermined sounds to notify the clinician of the sensor data received by the sensors of the electrosurgical or microwave system.

The invention claimed is:

1. A surgical system, comprising:
    a power supply for supplying electric energy;
    a surgical instrument;
    a power stage coupled to the power supply for converting the electric energy to a power signal, the power stage configured to transmit the power signal to the surgical instrument;
    an audio output device;
    a temperature sensor configured to sense a temperature of the surgical instrument; and
    a controller coupled to the power stage, the audio output device, and the temperature sensor, the controller configured to cause:
        the audio output device to output a first audio signal in response to the sensed temperature of the surgical instrument increasing to a first threshold temperature during use of the surgical instrument to perform a surgical procedure;
        the power stage to terminate transmitting of the power signal to the surgical instrument in response to the sensed temperature of the surgical instrument increasing to the first threshold temperature;
        the audio output device to output a second audio signal in response to the sensed temperature of the surgical instrument decreasing from the first threshold temperature to a second temperature threshold while the transmitting of the power signal to the surgical instrument is terminated;
        the power stage to initiate transmitting of the power signal to the surgical instrument in response to the sensed temperature of the surgical instrument decreasing to the second threshold temperature;
        the audio output device to output a third audio signal at a first rate in response to a rate at which the surgical instrument is advanced during the surgical procedure being less than a predetermined rate; and
        the audio output device to output the third audio signal at a second rate in response to the rate at which the surgical instrument is advanced during the surgical procedure being greater than the predetermined rate.

2. The surgical system of claim 1, wherein the controller is configured to monitor a duration of time during the surgical procedure and output sensory feedback based on the duration of time.

3. The surgical system of claim 2, wherein, in response to determining that the duration of time is greater than a predetermined threshold, the controller causes the audio output device to output a fourth audio signal.

4. The surgical system of claim 1, wherein the first audio signal is output at a first audio frequency and the second audio signal is output at a second audio frequency different than the first audio frequency.

5. The surgical system of claim 1, wherein at least one of the first or second audio signals is output as a tone that increases in frequency within a frequency spectrum.

6. The surgical system of claim 1, wherein at least one of the first or second audio signals is output as a tone that increases in volume.

7. The surgical system of claim 1, wherein the rate at which the third audio signal is output is based on a rate at which the surgical instrument is advanced along a predetermined trajectory.

8. The surgical instrument according to claim 1, wherein the rate at which the third audio signal is output is based on a rate at which the surgical instrument is retracted through a track disposed along a predetermined trajectory through an ablation target while the surgical instrument is ablating the track.

9. An electrosurgical system, comprising:
    an electrosurgical instrument
    a power stage configured to transmit electrosurgical energy to a radiator of the electrosurgical instrument;
    an audio output device;
    a sensor configured to sense the electrosurgical energy transmitted to the radiator and the transmitted electrosurgical energy reflected from the radiator; and
    a controller operably coupled to the sensor, the controller causing configured to cause:
        the audio output device to output a first audio signal and a second audio signal during operation of the power stage based on a first sensor signal and a second sensor signal received from the sensor during use of the electrosurgical instrument to perform a surgical procedure, wherein the first sensor signal is based on the sensed electrosurgical energy reflected from the radiator exceeding a first threshold and the second sensor signal is based on the sensed electrosurgical energy transmitted to the radiator line exceeding a second threshold;
        the audio output device to output a third audio signal at a first rate in response to a rate at which the electrosurgical instrument is advanced during the surgical procedure being less than a predetermined rate;
        the audio output device to output the third audio signal at a second rate in response to the rate at which the electrosurgical instrument is advanced during the surgical procedure being greater than the predetermined rate; and
        the power stage to control transmitting of the electrosurgical energy to the electrosurgical instrument in response to at least one of the first or second sensor signals.

10. The electrosurgical system of claim 9, wherein the first audio signal has a first audio frequency and the second audio signal has a second audio frequency different from the first audio frequency.

11. The electrosurgical system of claim 9, wherein the rate at which the third audio signal is output is based on a rate at which the electrosurgical instrument is advanced along a predetermined trajectory.

12. The electrosurgical system of claim 9, wherein the rate at which the third audio signal is output is based on a rate at which the electrosurgical instrument is retracted through a track disposed along a predetermined trajectory through an ablation target while the electrosurgical instrument is ablating the track.

13. A microwave ablation system, comprising:
    a microwave ablation device;
    a generator configured to deliver microwave energy to the microwave ablation device;

a temperature sensor operably coupled to the generator and configured to sense a temperature of the microwave ablation device; and an audio output device operably coupled to the generator and configured to:

output a first audio signal in response to the sensed temperature of the microwave ablation device increasing to a first threshold temperature during use of the microwave ablation device to ablate tissue;

output, subsequent to the first audio signal, a second audio signal in response to the sensed temperature of the microwave ablation device decreasing from the first threshold temperature to a second temperature threshold;

output a third audio signal at a first rate in response to a rate at which the microwave ablation device is advanced being less than a predetermined rate; and output the third audio signal at a second rate in response to the rate at which the microwave ablation device is advanced through the tissue being greater than the predetermined rate.

14. The microwave ablation system of claim 13, wherein the generator terminates delivery of the microwave energy to the microwave ablation device in response to the sensed temperature of the microwave ablation device increasing to the first threshold temperature.

15. The microwave ablation system of claim 14, wherein the generator initiates delivery of the microwave energy to the microwave ablation device in response to the sensed temperature of the microwave ablation device decreasing from the first threshold temperature to the second threshold temperature while the delivery of the microwave energy to the microwave ablation device is terminated.

16. The microwave ablation system of claim 13, wherein the first audio signal is output at a first audio frequency and the second audio signal is output at a second audio frequency different than the first audio frequency.

17. The microwave ablation system of claim 13, wherein at least one of the first or second audio signals is output as a tone that increases in frequency within a frequency spectrum.

18. The microwave ablation system of claim 13, wherein at least one of the first or second audio signals is output as a tone that increases in volume.

19. The microwave ablation system of claim 13, wherein the rate at which the third audio signal is output is based on a rate at which the microwave ablation device is advanced along a predetermined trajectory.

20. The microwave ablation system of claim 13, wherein the rate at which the third audio signal is output is based on a rate at which the microwave ablation device is retracted through a track disposed along a predetermined trajectory through an ablation target while the microwave ablation device is ablating the track.

* * * * *